US00PP28868P3

(12) United States Plant Patent
Giesen

(10) Patent No.: US PP28,868 P3
(45) Date of Patent: Jan. 9, 2018

(54) ***LOBELIA* PLANT NAMED 'LOBZ0011'**

(50) Latin Name: ***Lobelia erinus* L.**
Varietal Denomination: LOBZ0011

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 38 days.

(21) Appl. No.: 14/999,632

(22) Filed: Jun. 7, 2016

(65) Prior Publication Data

US 2017/0013767 P1 Jan. 12, 2017

(51) Int. Cl.
*A01H 5/02* (2006.01)

(52) U.S. Cl.
USPC ..... Plt./451

(58) Field of Classification Search
USPC ..... Plt./451
See application file for complete search history.

(56) References Cited

PUBLICATIONS

UPOV hit on *Lobelia* plant named 'LOBZ0011', QZ PBR 45512, filed Jul. 8, 2015.*

* cited by examiner

*Primary Examiner* — Anne M Grunberg
(74) *Attorney, Agent, or Firm* — Dale Skalla

(57) ABSTRACT

A new *Lobelia* plant named 'LOBZ0011' particularly distinguished by large, blue flowers with an white eye, strong stems with long inflorescences, dark green foliage, small sized leaves, medium sized plant size, free branching and an upright plant habit.

2 Drawing Sheets

Latin name of the genus and species of the plant claimed: *Lobelia erinus* L.
Varietal denomination: 'LOBZ0011'.

BACKGROUND OF THE NEW PLANT

The present invention comprises a new and distinct cultivar of *Lobelia*, botanically known as *Lobelia erinus*, and hereinafter referred to by the cultivar name 'LOBZ0011'.

'LOBZ0011' is a product of a planned breeding program. The new cultivar has large, blue flowers, strong stems with long inflorescences, dark green foliage, narrow leaves, free branching, and a medium sized, compact dense and upright plant habit.

'LOBZ0011' originated from a hybridization made in May 2011 in Andijk, The Netherlands. The female parent was an unpatented, proprietary *Lobelia* plant designated 'LOB08-294-1', having larger dark blue flowers, lighter green leaves and a trailing plant habit, while plant habit of 'LOBZ0011' is distinctly more upright.

The male parent of 'LOBZ0011' was the proprietary *Lobelia* plant designated 'LOB7-182-1', unpatented, having light blue flowers with an eye, more dark green and foliage, and thinner stems than 'LOBZ0011'.

The resulting seeds were sown in June 2011 and 'LOBZ0011' was selected as one flowering plant within the progeny of the stated cross in September 2011 in a controlled environment in Andijk, the Netherlands.

The first act of asexual reproduction of 'LOBZ0011' was accomplished when vegetative cuttings were propagated from the initial selection in the summer of 2012 in a controlled environment in Andijk, the Netherlands.

BRIEF SUMMARY OF THE INVENTION

Horticultural examination of plants grown from cuttings of the plant initiated in the spring of 2014 in Andijk, The Netherlands, and continuing thereafter, has demonstrated that the combination of characteristics as herein disclosed for 'LOBZ0011' are firmly fixed and are retained through successive generations of asexual reproduction.

'LOBZ0011' has not been observed under all possible environmental conditions. The phenotype may vary significantly with variations in environment such as temperature, light intensity and day length.

A Plant Breeder's Right for this cultivar was applied for with the European Union on Jul. 8, 2015, No. 2015/1570. 'LOBZ0011' has not been made publicly available more than one year prior to the filing of this application.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

Figure 1:
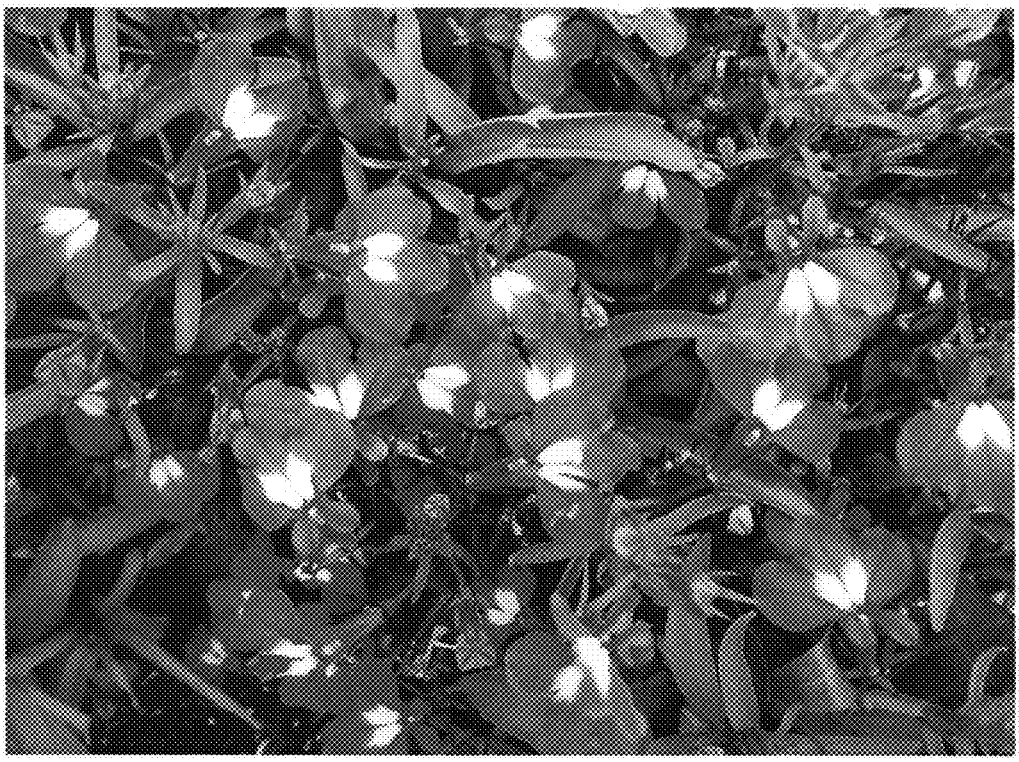
Figure 2:
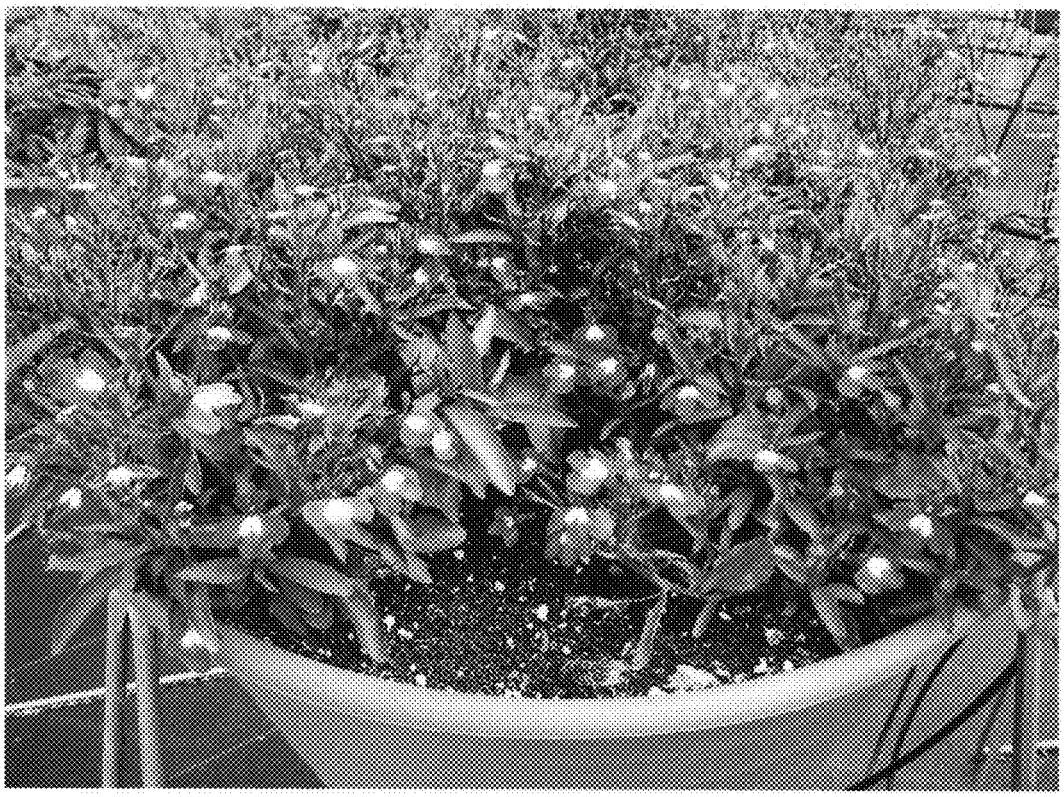

The accompanying photograph drawings show typical flower and foliage characteristics of 'LOBZ0011' with colors being as true as possible with an illustration of this type. The photograph drawings show in FIG. 1 a close-up of the flowers and in FIG. 2 a flowering potted plant of the new variety.

DETAILED BOTANICAL DESCRIPTION

The aforementioned photographs were taken in April 2014 from plants grown in a greenhouse trial in Andijk, The Netherlands. These plants were grown in 10.5 cm pots and were approximately 11 weeks of age. The close-up photograph was taken at the same time.

The observations and measurements were taken in Andijk, The Netherlands on Sep. 5, 2014, on 19-20 week old plants that were growing outdoors in 45 cm containers. Culture of these plants had started in mid April 2014 with the planting of rooted cuttings, 5 plants per container, and pinching about two weeks later.

Color references are made to The Royal Horticultural Society Colour Chart (R.H.S.), 2001.

TABLE 1

DIFFERENCES BETWEEN THE NEW VAREITY 'LOBZ0011' and A MOST SIMILAR VARIETY

| | 'LOBZ0011' | Commercially known as 'Techno Blue' |
|---|---|---|
| Flower color: | Blue with an small white eye | Blue |
| Leaf size: | Large broader leafs | Small leafs |
| Flower, diameter: | Larger: 2.01 cm | Smaller: 1.3 cm |
| Plant habit: | Upright, compact plant | Trailing plant |

Plant:

*Growth and habit.*—Vigorous growth habit; dense, and freely branching with medium internodes, Upright plant habit.

*Height.*—About 11 to 13 cm (from top of soil).

*Height (inflorescence included).*—About 25 cm.

*Width (horizontal diameter).*—From 25 to 40 cm.

*Branching characteristics.*—8 main stems, each with 3 to 4 secondary branches.

*Time to produce a finished flowering plant.*—About 10 weeks for a 12 cm pot.

*Garden performance.*—Used as patio planters, in mixed container plantings, or in garden beds.

*Time to initiate and develop roots.*—21-28 days at 20-23° Centigrade.

Roots:

*Number of days to initiate roots.*—About 15 days at about 22 degrees C.

*Number of days to produce a rooted cutting.*—21 to 25 days.

*Type.*—Fibrous and freely branching.

*Color.*—RHS N155A.

Foliage:

*Arrangement.*—Alternate.

*Leaf shape.*—Lanceolate.

*Apex.*—Mucronulate.

*Base.*—Attenuate.

*Margin.*—Entire to slightly incised.

*Leaf length.*—2.5-4.5 cm.

*Leaf width.*—0.6-0.9 cm.

*Immature leaf, color upper surface.*—RHS 135A.

*Immature leaf, color lower surface.*—RHS 136B.

*Mature color upper surface.*—RHS 145A.

*Mature color lower surface.*—RHS 146A.

*Venation type.*—Pinnate.

*Venation color, upper surface.*—Indistinct.

*Venation color, lower surface.*—Indistinct.

*Texture.*—Weak pubescence, both surfaces.

*Petiole.*—No petiole, leaves are sessile.

Stem:

*Characteristics.*—With slightly strengthened, protruding edges, side branches are developed at almost every node.

*Stem length.*—10-15 cm.

*Diameter.*—0.3-0.4 cm.

*Internode length.*—2.0-3.5 cm.

*Color.*—Mainly RHS 136B.

*Texture.*—Very sparsely hirsute.

Inflorescence:

*Type.*—Raceme, composed of single flowers in an alternate arrangement with one flower per node, subtended by a small leaflet.

*Blooming habit.*—Continuously through the growing season from spring to the fall.

*Quantity of inflorescences per plant.*—About 30 per container/15 per plant.

*Quantity of flowers per inflorescence.*—Up to 15 open flowers, and additional buds.

*Lastingness of individual blooms on the plant.*—3-7 days, depending on temperature.

*Fragrance.*—None.

*Inflorescence length.*—1.8-2.1 cm.

Peduncle:

*Color.*—From RHS 145B to RHS 145A.

*Length.*—6-7 cm.

*Diameter.*—0.2 cm.

*Texture.*—Pubescent.

Pedicels:

*Color.*—RHS 147B.

*Length.*—1.3-1.6 cm.

*Diameter.*—0.1 cm.

*Texture.*—Pubescent.

Flower:

*Corolla type and shape.*—Single, zygomorphic; upper lip is formed by two small petals, lower lip has three larger petals; petals are fused at the base forming a relatively long funnel-shaped tube.

Flower bud:

*Shape.*—Oblong.

*Length.*—1.8-2.0 cm.

*Diameter.*—0.3-0.4 cm.

*Color (at tight bud).*—RHS 96C and RHS 97D.

Immature flower:

*Main color upper surface.*—RHS 96B.

*Main color lower surface.*—RHS 97A for the top, RHS 197C at the base.

*Immature flower, width.*—1.1 cm.

Mature flower:

*Flower, (horizontal)length.*—2.1 cm.

*Flower, (horizontal)width.*—2.1 cm.

*Flower, vertical length (depth).*—2.2 cm.

*Color upper lip, upper surface.*—RHS 96B.

*Color upper lip, lower surface.*—RHS 96C.

*Upper petal lobes, length (from the tube opening).*—1.1-1.2 cm.

*Upper petal lobes, width.*—0.3-0.4 cm.

*Color lower lip, upper surface.*—RHS 96B.

*Color lower lip, lower surface.*—RHS 96C.

*Nectaries at base of lower petals.*—RHS 145B.

*Lower petal lobes, length (from the corolla opening).*—1.1-1.4 cm.

*Lower petal lobes, width.*—0.7-1.0 cm.

*Tube, color (outside).*—RHS 157B.

*Tube length.*—0.9-1.0 cm.

*Tube width.*—0.3-0.4 cm.

Petal (lobes):

*Shape.*—Obovate.

*Apex shape.*—Acute.

*Base.*—Fused.

*Margin.*—Entire.
*Texture upper surface.*—Glabrous.
*Texture lower surface.*—Short hair, mainly along the mid vein.

Calyx:
*Shape.*—5 sepals in a whorl, slanting outwards, fused at the base.
*Sepal color.*—RHS 138A.
*Sepal length* (*free ends*).—0.8 cm, respective 1.1 cm when including the funnel shaped part.
*Width.*—0.2 cm.
*Shape.*—Ligulate.
*Apex.*—Acute.
*Base.*—Fused.
*Texture.*—Pubescent.

Reproductive organs:

Stamens:
*Quantity.*—5.
*Filament, color.*—RHS 155B.
*Filament length.*—0.5-0.7 cm.
*Filament, diameter.*—0.1 cm.
*Anther color.*—RHS 187A.
*Anther length.*—0.2 cm.
*Pollen amount.*—Little.
*Pollen color.*—RHS 3B to RHS 3C.

Pistil:
*Quantity per flower.*—1.
*Length.*—1.0 cm.
*Stigma color.*—RHS 148B.
*Stigma length.*—0.2 cm.
*Style color.*—RHS 145B.
*Style length.*—From 0.7-0.8 cm.

Fruit and seed set: Occasionally observed outdoors.

Disease and insect resistance: Resistance and susceptibility typical for the species, no special observations made.

What is claimed is:

1. A new and distinct cultivar of *Lobelia* plant named 'LOBZ0011' as illustrated and described herein.

* * * * *